(12) United States Patent
Rao et al.

(10) Patent No.: US 7,982,074 B2
(45) Date of Patent: Jul. 19, 2011

(54) PROCESS FOR THE PREPARATION OF 1,1,1,2-TETRAFLUOROETHANE

(75) Inventors: Jampani Madhusudana Rao, Andhra Pradesh (IN); Shanthan Pamulaparthy Rao, Andhra Pradesh (IN); Siva Attaluri Prasad, Andhra Pradesh (IN); Banda Narasaiah, Andhra Pradesh (IN); Narayan Sripathi Reddy, Andhra Pradesh (IN); Radhakrishnan Kuppusamy, Andhra Pradesh (IN); Vijayakumar Veeramachaneni, Andhara Pradesh (IN); Patil Kamalakar Sukhadeorao, Andhra Pradesh (IN); Rambabu Yadla, Andhra Pradesh (IN); Koosampally Srinivas, Andhra Pradesh (IN); Leelakrishna Kondaveti, Andhra Pradesh (IN)

(73) Assignee: Council of Scientific & Industrial Research, Andhra Pradesh (IN)

( * ) Notice: Subject to any disclaimer, the term of this patent is extended or adjusted under 35 U.S.C. 154(b) by 184 days.

(21) Appl. No.: 11/643,767

(22) Filed: Dec. 22, 2006

(65) Prior Publication Data

US 2007/0106100 A1    May 10, 2007

Related U.S. Application Data

(63) Continuation of application No. 10/239,823, filed as application No. PCT/IN00/00042 on Mar. 31, 2000, now abandoned.

(51) Int. Cl.
  *C07C 19/08* (2006.01)
  *C07C 17/21* (2006.01)
  *C07C 17/20* (2006.01)
(52) U.S. Cl. ........................................ 570/161; 570/134
(58) Field of Classification Search ........................ None
  See application file for complete search history.

(56) References Cited

U.S. PATENT DOCUMENTS

| | | |
|---|---|---|
| 2,447,017 A | 12/1943 | Kearby |
| 2,606,159 A | 8/1952 | Owen |
| 2,885,442 A | 5/1959 | McCulloch et al. |
| 2,951,816 A | 9/1960 | Banks et al. |
| 3,179,602 A | 4/1965 | Gremillion |
| 3,277,019 A | 10/1966 | Young |
| 3,316,057 A | 4/1967 | Howk |
| 3,396,124 A | 8/1968 | Taylor et al. |
| 3,444,251 A | 5/1969 | Gardner |
| 3,470,262 A | 9/1969 | Mooi et al. |
| 3,794,588 A | 2/1974 | Stiles |
| 4,003,978 A | 1/1977 | Shiraishi et al. |
| 4,333,855 A | 6/1982 | Gardner et al. |
| 4,550,093 A | 10/1985 | Fanelli et al. |
| 4,565,831 A | 1/1986 | Wright et al. |
| 4,591,429 A | 5/1986 | Ho et al. |
| 4,721,558 A | 1/1988 | Jacobson et al. |
| 4,767,523 A | 8/1988 | Kukes et al. |
| 4,789,502 A | 12/1988 | Slaugh |
| 5,334,786 A * | 8/1994 | Koyama et al. ............... 570/168 |
| 5,449,656 A * | 9/1995 | Scott et al. ................... 502/307 |
| 6,007,700 A | 12/1999 | Alario et al. |

OTHER PUBLICATIONS

Rao, J. M., et al. "Effect of acid strength of co-precipitated chromia/alumina catalyst on the conversion and selectivity in the fluorination of 2-chloro-1, 1, 1-trifluoroethane to 1,1,1,2-tetrafluoroethane" Journal of Fluorine Chemistry, CH, Elsevier Sequoia, Lausanne, vol. 95, No. 1-2, Jun. 4, 1999, pp. 177-180.

* cited by examiner

*Primary Examiner* — Daniel Sullivan
*Assistant Examiner* — Yevegeny Valenrod
(74) *Attorney, Agent, or Firm* — Sughrue Mion, PLLC

(57) ABSTRACT

The present invention relates to a process for preparing a co-precipitated $Cr_2O_3/Al_2O_3$ catalyst promoted by Zinc, said process comprising co-precipatation of chromium and aluminum metal hydroxides from corresponding trivalent metal salt solutions using NH4OH, NaOH or KOH as a base and followed by calcination to give mixed oxide precatalyst in amorphous from which is impregnated with an activity promoting amount of Zinc compound. The catalyst is used for the preparation of HFC-134a by fluorination of trichloroethylene and fluorination of intermediate of the former reaction (HCFC-133a).

10 Claims, No Drawings

PROCESS FOR THE PREPARATION OF 1,1,1,2-TETRAFLUOROETHANE

This application is a continuation of U.S. patent application Ser. No. 10/239,823, filed on Sep. 03, 2003, now abandoned which is a National Stage application filed under §371 of PCT Application No. PCT/IN00/00042 filed Mar. 31, 2000, the entire disclosure of which is incorporated herein in its entirety.

FIELD OF THE INVENTION

This invention relates to a process for the preparation of co-precipitated chromia-alumina catalyst impregnated with zinc salt, and a process for the preparation of 1,1,1,2-tetrafluoroethane (designated as HFC-134a) using the said catalyst.

BACKGROUND OF THE INVENTION

It is known in the art that the catalytic vapor phase fluorination of haloalkanes with hydrogen fluoride results in the formation of fluorine rich haloalkanes. Aluminum fluoride is one of the catalysts known in the art for the halogen exchange. However a suitable catalyst is required for the fluorination of haloalkenes to give fluorine rich haloalkanes.

As U.S. Pat. No. 2,885,427 (1959) has found $CrF_3.3H_2O$ as a suitable catalyst for the fluorination of haloalkanes and haloalkenes, $CrF_3.3H_2O$ is only precatalyst which is oxygenated at 600° C. to obtain an active catalyst whose empirical formula was found to be $CrOF_3F_2$. The reaction of trichloroethylene (herein after referred to as TCE), with HF in vapor phase at 350° C. using the above catalyst gave 2-chloro-1,1,1-trifluoroethane (herein after designated as HCFC-133a) as the major component and HFC-134a as a minor component.

The formation of HFC-134a from TCE involves several steps. The first step is the addition of HF as per Markownikov's rule to give 1-fluoro-1,1,2-trichlorethane (HCFC-131a). Subsequently, the chlorine present in HCFC-131a will be successively replaced by fluorine via the intermediates 1,2-dichloro-1,1, difluoroethane (HCFC-132b), HCFC-133a to give finally HFC-134a. It is known in the art that the ease of replacement of chlorine bound to a carbon, by fluorine follows the order trihalide (—CX3)>dihalide (—CHX2)>primary halide (—CH$_2$X) where X=Cl. In the specific case of the catalytical fluorination of TCE a very high yield of HCFC-133a is obtained. However, the replacement of the primary halide present in HCFC-133a requires an efficient catalyst and relatively higher temperature to get good conversions and high selectivity, which are important for commercial preparation. It thus became necessary to divide the fluorination of TCE into two stages. The first stage involves fluorination of TCE to give HCFC-133a. The second stage involves the fluorination of HCFC-133a to give HFC-134a. UK Patent GB 2,030,981 A (1979) reported the fluorination of HCFC-133a at 400° C. using $CrF_3.3H_2O$ as a precatalyst. The catalyst was activated by treatment first with air and then with a mixture of HF and air. After activation and during the initial period of fluorination, HCFC-133a and HF in a mole ratio of 1:6 were passed over the catalyst to obtain 31% conversion and 98% selectivity for HFC-134a. Subsequently, the reaction was continued by introducing additionally air during which time both conversion and selectivity started falling gradually.

The discovery of oxygenated $CrF_3.3H_2O$ as a precatalyst lead to the development of several new catalysts based on the oxides of Chromium, Nickel, Cobalt, Aluminum etc. The patents U.S. Pat. No. 3,752,850 (1973), U.S. Pat. No. 3,859, 424 (1975), described the use of $Cr(OH)_3$ or $Cr_2O_3.XH_2O$ as a precatalyst which is activated by a process of calcination followed by fluorination with HF. The fluorination of TCE to give HCFC-133a was carried out at atmospheric pressure using a HF:TCE mole ratio of 6:1. The best conversion and selectivity were obtained at temperatures in the range 300° C.-340° C. The yield of HCFC-133a was 93%. The patents U.S. Pat. No. 3,755,477 (1973), U.S. Pat. No. 4,129,603 (1978) and U.S. Pat. No. 4,158,675 (1979) report a fluorination catalyst prepared by the sequence of precipitation of $Cr(OH)_3$ from $Cr^{3+}$ salts using a base, steam treatment at 95° C., dehydration, calcination and HF treatment. The U.S. Pat. No. 3,755,477 reports a yield of 85% HCFC-133a using HF:TCE in mole ratio 6:1 at 300° and atmospheric pressure. The U.S. Pat. Nos. 4,129,603 and 4,158,675 claim a highest conversion of 18.2% in the fluorination using HF:HCFC-133a in mole ratio 3:1, at a reaction temperature in the range 335°-355° C. and atmospheric pressure. The selectivity for HFC-134a was 91%.

There have been further modifications in the preparation of the precatalyst based on chromium hydroxide. The European Patent 0514932 (1992) described the preparation of $Cr(OH)_3$ from $Cr(NO_3)_3$ with different surface areas in the range 48-180 $m^2$/g and used graphite as an additive. This catalyst gave a maximum conversion of 20.3% with a selectivity of 95.7% for HFC-134a using HF:HCFC-133a in mole ratio 4.6:1, at a reaction temperature of 330° C. and a space velocity of 2250/h.

The EP 0546883 (1992) reported the preparation of chromia with or without Ni compound using sol gel technique. The addition of Nickel compound has improved the life of the catalyst.

The patents EP0486333 A1 (1991) and EP 0554165 A1 (1993) reported a catalyst containing chromia/Nickel salt impregnated on partially fluorinated Alumina or $AlF_3$. The fluorination of HCFC-133a was carried out under pressure and in the presence of oxygen, to give HFC-134a with a maximum conversion of 21% and 99% selectivity.

The EP 0641598 A2 (1994) discloses a process for the fluorination catalyst by firing Cr(III) hydroxides in hydrogen atmosphere. The catalyst obtained was crystalline $Cr_2O_3$. The catalyst prepared in this Patent contains two stages using a mole ratio of HF:TCE 15:1 a conversion of 91.2% TCE and 95.3% selectivity for HCFC-133a was obtained. In the second stage using a mole ratio of HF:HCFC133a (8:1) a conversion of 19.8% HCFC-133a and 99.3% selectivity for HFC-134a was obtained. The catalyst obtained by the method of this invention has only two elements. The catalyst is crystalline and co-precipitation occurs at lower dilutions. On the other hand, the catalyst of the present invention contains three elements (Cr/Al/Zn) in which $ZnCl_2$ is impregnated on a co-precipitated Chromia/Alumina catalyst, the catalyst is amorphous and co-precipitation has been done at higher dilutions.

The U.S. Pat. No. 4,792,643 (1988) Patent discloses a methodology for the preparation of HFC-134a starting from HCFC-133a using a catalyst prepared by co-extrusion of Aluminum oxyhydroxide and chromium oxide. The preparation of HCFC-133a from TCE using a catalyst prepared by co-extruded catalyst impregnated with cobalt chloride. The Patent reports the preparation of different catalyst by impregnation of $CrO_3$, $TiCl_4$, $CrCl_3$, $CoCl_2$ and $NiCl_2$ on porous activated alumina. These catalysts were used to obtain directly HFC-134a by fluorination of TCE. The conversions of TCE and the combined selectivities for HFC-134a and HCFC-133a are low for large-scale preparations. In short, this patent described a methodology for the preparation of co-deposition of chromia and a compound of transition metal (Ti, Zr, Mo, Mg, Co, Ni) on alumina simultaneously or sequentially. This invention is also different from the present invention.

The U.S. Pat. No. 5,155,082 (1992) described a methodology for the preparation of co-deposition of chromia and a compound of transition metal (Ti, Zr, Mo, Mg, Co, Ni) on alumina simultaneously or sequentially. The Patent discloses a catalyst prepared by blending Al(OH)$_3$ and chromium oxide in the presence of a solvent. This catalyst after calcination and fluorination was used in the reactions of HF, separately with TCE and HCFC-133a under pressure. In the case of TCE, high selectivity for HCFC-133a was reported although no values were given. The fluorination of HCFC-133a was reported to give 18% conversion with 94% selectivity for HFC-134a. In short, the above Patent discloses a methodology for the preparation of HFC-134a starting from HCFC-133a using a catalyst prepared by co-extrusion of Aluminum oxyhydroxide and chromium oxide. The preparation of HCFC-133a from TCE using a catalyst prepared by co-extrusion of aluminum oxyhydroxide/chromium oxide or the co-extruded catalyst impregnated with cobalt chloride. This invention is entirely different from the present process especially in co-extrusion or co-deposition catalyst.

The EP 0328127 A1 (1989) reports the use of a catalyst obtained by impregnation of compounds of Co, Mn, Ni, Pd, Ag and Ru on alumina or AlOF as a precatalyst for the fluorination of HCFC-133a. The catalyst obtained from CoCl$_2$/Al$_2$O$_3$ gave conversion of 33.5% with selectivity 93.7% for HFC-134a in the fluorination of HCFC-133a using HF containing ppm levels of oxygen. The above catalyst has been further modified in Indian Patent 172054 (1989) by using additives selected from compounds of metals having atomic number 58-71. At temperature above 350° C. and using HF:HCFC-133a mole ratio in the range 10:1 to 20:1, conversions in the range 30-40% were obtained. At higher temperatures the conversions were higher but the selectivity dropped to 82.9%.

The patents WO 92/16480 (1992) and WO 92/16481 (1992) disclosed a new catalyst prepared by impregnation of zinc compound on Al$_2$O$_3$ and optionally containing one or more other metal selected from this group with atomic number 57-71. This catalyst was used for fluorination of TCE and also HCFC-133a to obtain very high selectivities for HCFC-133a and HFC-134a respectively. However, very high contact times are required in the fluorination of TCE.

Another publication to Rao J. M. et al teaches the effect of acid strength of co-precipitated chromia/alumina catalyst on the conversion and selectivity in the fluorination of 2-chloro 1,1,1-trifluoroethane to 1,1,1,2-tetrafluoroethane. (Journal of Fluorine Chemistry 95, pp. 177-180 Elsevier Science 1999). The present invention is entirely different and not related to subject matter disclosed by this document. An examination of TPR data reveals a difference in reduction pattern in terms of T-$_{max}$ variation and also hydrogen uptake per mmol.g$^{-1}$. This data further supports the increased number in the availability of reducible group in the catalyst B of the present invention in comparison to catalyst B of Rao et al, thereby providing enhanced selectivity and efficacy in the formation of the required product 1,1,1,2-tetrafluoroethane in the present invention.

The use of compounds of zinc and/or magnesium as promoters on chromium based catalyst impregnated on Alumina or AlF$_3$ was reported in the EP 0502605 A1 (1992). In fluorination using HF:TCE in a mole ratio of 10:1, a conversion of only 40.9% was reported at 310° C. and contact time of 1 sec. The same catalyst gave a conversion of 20.5% with a selectivity>99% in the fluorination using HF:HCFC-133a in mole ratio 3.5:1 at reaction temperature of 330° C. and contact time 2 sec.

OBJECTS OF THE INVENTION

The main objective of the present invention is to provide a process for the preparation of co-precipitated chromium-aluminum catalyst impregnated with zinc chloride. Another objective is to provide a process for the preparation of HFC-134a by the fluorination of trichloroethylene.

Another objective of the invention is to reduce the relative percentage of strong acid sites in the catalyst in order to achieve high selectivity.

Another objective is to provide enough crushing strength to the catalyst for use under pressure.

DETAILED DESCRIPTION OF THE INVENTION

Accordingly, the present invention relates to a process for preparing a coprecipitated Cr$_2$O$_3$/Al$_2$O$_3$ catalyst promoted by zinc, said process comprising coprecipitation of chromium and aluminum metal hydroxides from corresponding trivalent metal salt solutions using NH$_4$OH, NaOH or KOH as a base and followed by calcination to give mixed oxide precatalyst in amorphous form which is impregnated with an activity promoting amount of Zinc compound, wherein the chromium metal hydroxide used in a bulk chromia.

Another embodiment of the invention relates to a process for the manufacture of 1,1,1,2-tetrafluoroethane (HFC-134a), which comprises:
(a) fluorination of trichloroethylene (TCE) with AHF by contacting with a co-precipitated Cr$_2$O$_3$/Al$_2$O$_3$ catalyst promoted by Zinc salt and as produced by a method defined above, to give the intermediate 2-chloro 1,1,1,-trifluoroethane (HCFC-133a), and
(b) fluorination of HCFC-133a with AHF by contacting with a co precipitated Cr$_2$O$_3$/Al$_2$O$_3$ catalyst promoted by Zinc salt as defined above, to give HFC 134a.

In one embodiment, the invention provides a process for the preparation of 1,1,1,2-tetrafluoroethane which comprises the step of contacting a gas phase feed consisting of trichloroethylene and AHF with chromia alumina ZnCl$_2$ catalyst at a temperature in the range of 275° C. to 400° C., optionally under pressure and recovering 2-chloro-1,1,1-trifluoroethane (HCFC-133a).

In another embodiment, the invention provides a process, which comprises contacting a gas phase feed consisting of 2-chloro-1,1,1-trifluoroethane and HF on co-precipitated chromia-alumina impregnated with zinc chloride catalyst as defined above, at a temperature in the range of 275°-400° C. under pressure and recovering 1,1,1,2-tetrafluoroethane in a conventional manner from the product stream.

In yet another embodiment, the co-precipitated chromia alumina catalyst may contain chromium-aluminum in the atomic ratio 1:1 to 1:14 and the amount of zinc compound used for impregnation of co-precipitated Chromia/Alumina catalyst ranges from 2-12% by weight.

Preferably, the mole ratio of anhydrous hydrogenfluoride and trichloroethylene is in the range of 6:1 to 12:1 and the mole ratio of anhydrous hydrogenfluoride and 2-chloro-1,1,1-trifluoroethane in the range 4:1 to 15:1.

In another embodiment, the ratio of the catalyst to feed (W/F) is in the range 65-150 g.h/mole and the contacting of the gas feed with the catalyst is carried at a pressure in the range of 15-210 psig.

The commercial process for HFC-134a uses trichloroethylene (TCE) and anhydrous hydrogen fluoride as raw materials. The addition of HF to TCE and the subsequent exchange of chlorine by fluorine require presence of a suitable catalyst to achieve maximum atom economy. The process is conveniently divided into the following two stages:
Stage-I: Fluorination of TCE to give HCFC-133a
Stage-II: Fluorination of HCFC-133a to give HFC-134a The process can be carried out both at atmospheric pressure and under pressure. The process under pressure has the advantage of directly feeding the product stream into distillation columns operating under pressure for the separation of the desired product and by products and to recover and recycle the un-reacted starting materials and intermediates.

The factors that influence the conversion and selectivity are given below:
1. The precatalyst and its activation with HF.
2. Mole ratio of HF:TCE and HF:HCFC-133a.
3. Reaction temperatures
4. The ratio of weight of the catalyst, to the number of moles per hour in the feed expressed as W/F g.h/mole.
5. Pressure.

The catalytic activity in the halogen exchange has been attributed to the Lewis acid centers. In the case of chromia based catalyst the activity was attributed to the number of reversibly oxidizable sites in the precatalyst. In the alumina-based catalyst the formation of $\beta$-$AlF_3$ during activation is critical to the catalytic activity. The catalysts based on chromia alone were found quite efficient in fluorination at atmospheric pressures. Under pressure this catalyst exhibited a fall in the conversion and selectivity. Also volatile compounds are generated that condense at the reactor exit causing blockage, a serious draw back for commercial operation. The use of graphite to increase the strength of the catalyst resulted in a loss in activity.

This invention takes advantage of the catalytic activity of both chromia and alumina and reports the preparation of a co-precipitated catalyst starting from salts of $Cr^{3+}$ and $Al(NO_3)_3$. The relative atomic ratios of Cr:Al can be in the range 1:1 to 1:14 preferably in the range 1:3 to 1:10 and most preferably in the range 1:3 to 1:5.

The co-precipitation is done by using a base selected from NaOH, KOH and $NH_4OH$, preferably with $NH_4OH$. The precipitation is carried out at various dilutions using the base of strength 1 to 6 molar, preferably 4-6 molar. The quantity of water used to dissolve the combined quantity of chromium (III) salt and aluminum nitrate are in the weight ratio 38:1 to 4:1 preferably 19:1 to 4:1 and most preferably 10:1 to 4:1. Total acidity of the precatalyst is known to depend upon the pH at which hydroxides are formed. The precipitation is completed by adjusting the final pH in the range 7-8 and the hydroxides are filtered, washed with water, dried to constant weight at a temperature in the range 70° C.-150° C., preferably in the range 70° C.-120° C. The dried catalyst is powdered and shaped into tablets or extrudes and calcined in nitrogen atmosphere at a temperature in the range 350° C.-400° C., preferably in the range 380° C.-400° C. for 24 to 48 hours. The shape of the catalyst has no effect on its activity.

The calcined catalyst was activated by treating sequentially with $N_2$ at 400° C. for 24 hours followed by fluorination in the temperature range 150° to 400° C. till the exit stream of HF contains less that 1% of moisture. The process also economizes on the use of the Cr compound as a raw material for the preparation of the catalyst thus minimizing the cost and problem related to effluent disposal of spent catalyst.

It was found that the performance of the co-precipitated $Cr_2O_3/Al_2O_3$ catalyst can be further improved by reducing the total acidity by impregnation or deposition with a compound of zinc. The addition of zinc compound results in suppressing the formation 2-chloro-1,1,1,2-tetrafluoroethane (HCFC-124), pentafluoroethane (HFC-125) and 1,1,1-trifluoroethane (HFC-143a) in the fluorination of both TCE and HCFC 133a. The addition of a zinc compound on $Cr_2O_3/Al_2O_3$ reduced the percentage of strong acid centers relative to the weak and medium acid centers as revealed by TPD of ammonia. The quantity of zinc compound taken is to give a zinc content of 2-12%, preferably in the range 3-7% by weight of co-precipitated $Cr_2O_3/Al_2O_3$ catalyst.

The stoichiometric ratio of HF:TCE required to give HCFC-133a is 3:1. It is found that excess of HF is required to obtain maximum conversions and selectivity. The ratio of HF:TCE should be in the range 6:1 to 12:1 preferably in the range 7:1 to 10:1. Similarly, in the fluorination of HCFC-133a to HFC-134a the ratio of HF:HCFC-133a should be in the range 4:1 to 15:1, preferably in the range 6:1 to 10:1.

The fluorination of TCE to give HCFC-133a is a multi-step reaction. The degree of conversion and selectivity depends on the residence time, which determines the W/F value. It was found that the preferred W/F value is in the range 65-150 and most preferably in the range 70-100. Similarly, in the fluorination of HCFC-133a to give HFC-134a, the preferred W/F value is in the range 80-150, most preferably in the range 100±5.

Pressure was found to have an effect in the fluorination of HCFC-133a to HFC-134a. Under the same set of conditions of temperature, mole ratio and W/F, the conversions were higher at atmospheric pressure compared to the reaction under pressure. It was found advantageous to carry out both the stages of fluorination under pressure keeping in view the separation of different components in the product mixture. The required pressure was found to be in the range 70-210 psig.

It was found that the fluorination of TCE and HCFC-133a could be carried out in the temperature range 275°-400° C. and preferably in the range of 300°-375° C. to obtain good conversions and selectivity to the desired product.

A key feature of this invention is that a single catalyst is useful for both stages of the reaction to give high selectivity and optimum conversions.

The preparation of the precatalyst, its activation and use in the fluorination of TCE to give HFC-134a have been illustrated in the example given below:

EXAMPLES

Catalyst Preparations

All chemicals used are of commercial grade. De-mineralized water was used throughout.
Catalyst A: $Cr_2O_3/Al_2O_3$ Catalyst:
341 g $Cr(NO_3)_3.9H_2O$ and 1440 g Al $(NO_3)_2.9H_2O$ were dissolved in 8600 g water at room temperature. The solution is kept under stirring and 10% ammonia solution is added at a uniform rate of 1300 g/h till the pH attains 7.5. The slurry obtained is charged into an autoclave and heated at 90° C. for 2 h and cooled to 50° C. The resulting slurry was filtered and washed with water. The cake obtained was divided into two portions in weight ratio 3:1. The major portion was dried for 2 h at 70° C. and then at 120° C. till constant weight. The dried cake was powdered to a particle size>125 mesh. The second portion was partially dried at 70° C. and mixed with the powder of major portion and extruded into 2.5 mm die pellets or extruded using standard procedures. The extrudes were calcinated at 400° C. for 24 h in $N_2$ atmosphere to get 262 g of co-precipitated catalyst designated as catalyst-A. The catalyst is X-ray amorphous.

Catalyst B: $ZnCl_2/Cr_2O_3/Al_2O_3$:

100 g of extrudes of catalyst 'A' were suspended for 1 h in a solution obtained by dissolving 15.4 g $ZnCl_2$ in 89.0 g water. The mixture was filtered by gravity and the solids were dried at 120° C. to constant weight to give 110 g of the impregnated catalyst $ZnCl_2/Cr_2O_3/Al_2O_3$. X-ray revealed the amorphous nature of the catalyst. The zinc content with catalyst was found to be 4.3 wt %.

Catalyst C: $ZnCl2/Cr_2O_3/A_2O_3$.

157.35 g $Cr(NO_3)_3.9H_2O$ and 532.7 g $Al(NO_3)_3.9H_2O$ were dissolved in 25.75 Kg water. 1.7% of ammonia solution was added at a uniform rate over a period of 18-25 h to the above solution, kept under stirring till the precipitation is complete and the final pH reaches 7.5. The slurry is filtered, washed with water and dried at 120° C. till constant weight to obtain 116.7 g of the catalyst.

50 g of the above catalyst was powdered and mixed with a solution of 4.17 g of $ZnCl_2$ in 55 g of water. The mixture is hanged on a rotavapor and water is removed by slow vaporization to dryness. The solid obtained is shaped into 3-mm tablets and calcined at 400° C. in $N_2$ atmosphere for 24 h to obtain 40.5 g of catalyst C. The X-ray showed the amorphous nature of the catalyst.

Catalyst D: $ZnCl_2/Cr_2O_3/Al_2O_3$ 157.35 g $Cr(NO_3)_3.9H_2O$ and 532.7 $Al(NO_3)_3.9H_2O$ were dissolved in 12.89 kg water. Ammonia solution (5%) was added at a uniform rate over a period of 18-25 h to the above solution, kept under stirring till the precipitation is complete and the final pH attains 7.5. The slurry is filtered, washed with water and dried at 120° C. till constant weight to obtain 128.7 g of the base catalyst.

The above catalyst 50 g was powdered and mixed with a solution of 4.5 g of ZnCl2 in 45 g of water. The subsequent workup was done as in the case of catalyst C to obtain 39.5 g of catalyst D. The X-ray showed the amorphous nature of the catalyst.

Catalyst E: $ZnCl_2/Cr_2O_3/Al_2O_3$

A mixture of 157.35 g $Cr(NO_3)_3.9H_2O$ and 532.7 g $Al(NO_3)_3.9H_2O$ was dissolved in 6.45 Kg of water. The precipitation was done by adding 1.7-% ammonia solution at a constant rate over a period of 19.25 h to the above solution with constant stirring till the pH of the slurry attains 7.5. The slurry was filtered, washed with water and dried at 120° C. till constant weight to obtain 116.7 g of the catalyst.

50 g of the above catalyst was powdered and mixed with a solution of 4.5 g of $ZnCl_2$ in 45 g of water. The water was removed as described in the case of catalyst C. The dried catalyst was calcined at 400° C. for 24 h and shaped into tablets of 3 mm size to obtain 38.6 g of the catalyst E. The X-ray revealed amorphous nature.

Catalyst F: $ZnCl_2/Cr_2O_3/Al_2O_3$ 157.35 g of $Cr(NO_3)_3$, and 532.7 g of $Al(NO_3)_3.9H_2O$ were dissolved in 6.4 Kg of water. The precipitation was done by the addition of 1.7% ammonia solution over a period of 12 min. with constant stirring till the precipitation is completed and the final pH of slurry attained 7.5. The slurry was filtered, washed and dried at 120° C. till constant weight to obtain 136.5 g of the base catalyst.

50 g of the above catalyst was powdered and mixed with a solution of 4.16 g $ZnCl_2$ in 45 g of water. The water was removed as described in the case of catalyst C. The dried catalyst was calcined at 400° C. for 24 h and shaped into tablets of the size 3-mm to obtain 40.5 g of the catalyst F. The X-ray showed amorphous nature.

Catalyst G: $ZnCl_2/Cr_2O_3/Al_2O_3$

A solution of $Cr(NO_3)_3.9H_2O$ (157.35 g) and $Al(NO_3)_3.9H_2O$ (532.7 g) in 19.32 Kg. water was prepared to which 1.7% ammonia solution was added with constant stirring over a period of 18 h till the pH reaches 7.5. The slurry was filtered, washed and dried at 120° C. till constant weight to obtain 149.4 g of the catalyst.

50 g of the above catalyst was powdered and mixed with a solution of 4.5 g of $ZnCl_2$ in 45 g of water. The water was removed on rotavapor as described in the case of catalyst C and the solid was calcined at 400 degree C. for 24 h and shaped into tablets of 3 mm size to obtain 36 g of the catalyst G. The X-ray showed amorphous nature.

Catalyst H: $ZnCl_2/Cr_2O_3/Al_2O_3$ 58.41 g of $Cr(NO_3)_3.9H_2O$ and 197.9 g of $Al(NO_3)_3.9H_2O$ were dissolved in 1600 ml of $H_2O$. A 3.75% solution of ammonia was added at a uniform rate over a period of 7 h under stirring till the pH reaches 7.5. The slurry was filtered, washed with water and the wet cake obtained was transferred into an autoclave and mixed with 500 g of water. The mixture was stirred in a closed system for 6 h at 90° C. After completion of the thermal treatment, the slurry was cooled to 35° C. and filtered, washed with water and dried at 120° C. till constant weight to obtain 59.5 g $Cr_2O_3/Al_2O_3$ catalyst.

25 g of the above catalyst was powdered and mixed with a solution of 1-g of zinc chloride in 17 g of water. The water was removed on rotavapor and dried to obtain 27 g of the catalyst. The catalyst was shaped into tablets of 3-mm size and calcined at 400° C. for 24 h to get 18.67 g of catalyst H.

Catalyst I: $Cr_2O_3/Al_2O_3$

Following the procedure described for catalyst A the co-precipitated catalyst is prepared starting with 95 g of $Cr(NO_3)_3.9H_2O$ and 603 g, $Al(NO_3)_3.9H_2O$ dissolved in 3.4 Kg water and 10% ammonia solution to obtain 103 g of calcined catalyst-1.

Catalyst J: $ZnCl_2/Cr_2O_3/Al_2O_3$ 92 g of catalyst-A was suspended in a solution of 16.35-g zinc chloride in 100 g of water and the mixture was slowly vaporized to dryness on a rotavapor under vacuum. The product obtained was dried to constant weight at 120° C. to obtain 110 g of catalyst-J.

Catalyst K: $ZnCl_2/Cr_2O_3/Al_2O_3$ 92 g of catalyst A was suspended in a solution of 24.65 g of Zinc chloride in 100 g of water and the mixture was slowly vaporized to dryness on rotavapor under vacuum. The product obtained was dried to constant weight at 120° C. to obtain 119 g of catalyst-K.

Bulk Chromia Catalyst: $Cr_2O_3$.

The procedure described in Inorganic synthesis (1946) Vol. II, pp 190-191, was followed to reduce $CrO_3$ with ethanol to obtain CrOOH, which was filtered, washed with water, dried at 120° C. till constant weight. The product was powdered, shaped into 3-mm tablets and calcinated at 400° C. for 24 h in nitrogen atmosphere.

General Method of Fluorination:

The experimental set up consists of separate feed lines for HF and TCE or HCFC-133a, vaporizer and a 90 cm long 1" i.d. inconel tubular reactor, pressure relief trap, alkali scrubber, drier, condenser and a receiver cooled in dry ice-acetone mixture. A sample of the product stream is drawn periodically from a sampling valve between the drier and condenser. Electrically heated block furnaces and PID controllers maintain the temperatures in different zones.

The catalyst is loaded into the tubular reactor and pretreated with nitrogen at 400° C. for 24 h. The temperature is then lowered to 150° C. and a slow stream of HF is introduced along with nitrogen. After the initial exothermicity nitrogen is slowly withdrawn while raising the temperature of the catalyst bed to 375° C. The fluorination is continued until the moisture content in the exit HF is below 1%. The bed temperature of the catalyst is then brought and maintained at the reaction temperature and TCE or HCFC-133a is introduced into the system along with HF. The feed quantity of HF and TCE or HCFC-133a were adjusted to give the desired molar ratios and W/F. The product stream is scrubbed with aq. KOH solution and then condensed in a trap cooled in dry ice-acetone. The composition of the product stream is determined by GC after reaching steady state and is based on the peak areas. The fluorination experiments were carried out both at atmospheric pressure and under pressure as indicated in the examples given below:

Example-1

Fluorination of TCE at Atmospheric Pressure:

|  | Catalyst | | |
|---|---|---|---|
|  | Catalyst-A | Catalyst-B | Bulk Chromia |
| Reaction temperature ° C. | 300 | 300 | 300 |
| Mole ratio. HF/TCE | 7 | 6 | 6 |
| W/F., g · h/mole | 55 | 100 | 98 |
| Conversion of TCE % | 97 | 96.5 | 96 |
| Selectivity for HCFC-133a | 96.5 | 97.5 | 97.5 |
| Selectivity for HFC-134a, % | 2.0 | 1.0 | 1.0 |

Example-2

Fluorination of HCFC-133a to HFC-134a at Atmospheric Pressure.

|  | Catalyst | | |
|---|---|---|---|
|  | Catalyst-A | Catalyst-B | Bulk Chromia |
| Reaction temp. ° C. | 350 | 360 | 350 |
| Mole ratio. HF/TCE | 9 | 8 | 12 |
| W/F., g · h/mole | 100 | 100 | 113 |
| Conversion of TCE % | 27 | 22 | 32 |
| Selectivity for HFC-134a, % | 85 | 96 | 95 |

Example-3

Fluorination of TCE Under Pressure:

|  | Catalyst | | |
|---|---|---|---|
|  | Catalyst-B | | |
| Reaction temperature ° C. | 300 | 300 | 300 |
| Mole ratio, HF/TCE | 6 | 6 | 6 |
| Pressure, psig | 70 | 70 | 70 |
| W/F., g · h/mole | 100 | 70 | 50 |
| Conversion of TCE % | 99.0 | 97.5 | 96.5 |
| Selectivity for HCFC-133a | 95.5 | 97.0 | 95.3 |
| Selectivity for HFC-134a, % | 2.0 | 0.5 | 0.2 |

Example-4

Fluorination of HCFC-133a to HFC-134a Under Pressure:

|  | Catalyst | | |
|---|---|---|---|
|  | Catalyst-B | | |
| Reaction temp. ° C. | 355 | 330 | 330 |
| Mole ratio. HF/TCE | 6 | 6 | 4 |
| Pressure, psig | 70 | 70 | 70 |
| W/F., g · h/mole | 50 | 50 | 50 |
| Conversion for HCFC-133a, % | 35 | 19 | 15 |
| Selectivity for HFC-134a, % | 73 | 80 | 82 |

Example-5

Fluorination of HCFC-133a to HFC-134a Under Pressure:

|  | Catalyst | | |
|---|---|---|---|
|  | Catalyst-B | | |
| Reaction temp. ° C. | 360 | 360 | 360 |
| Mole ratio. HF/HCFC-133a, % | 8 | 6 | 6 |
| Pressure, psig | 70 | 70 | 70 |
| W/F, g · h/mole | 100 | 70 | 50 |
| Conversion for HCFC-133a, % | 24.0 | 22.0 | 14.4 |
| Selectivity for HFC-134a, % | 96.0 | 88.2 | 84.5 |

Example-6

Fluorination of TCE at Atmospheric Pressure Using Catalysts Prepared Under Different Dilutions.

|  | Catalyst | | | |
|---|---|---|---|---|
|  | Catalyst-C | Catalyst-D | Catalyst-E | Catalyst-F |
| Reaction temp. ° C. | 300 | 300 | 300 | 300 |
| Mole ratio, HF/HCFC-133a | 6 | 6 | 6 | 6 |
| W/F, g · h/mole | 100 | 100 | 100 | 100 |
| Conversion of TCE, % | 96.0 | 96.5 | 97.5 | 87.6 |
| Selectivity for HCFC-133a, and HFC-134a, % | 98.0 | 98.3 | 97.5 | 96.7 |

A key feature of this invention is that a single catalyst is useful for both stages of the reaction to give high selectivity and optimum conversions. The preparation of the precatalyst, its activation and use in the fluorination of TCE to give HFC-134a is illustrated in the example given below:

Examples: Catalyst Preparations. All chemicals used are of commercial grade. Demineralised water was used throughout.

Catalyst A: $Cr_2O_3/Al_2O_3$ Catalyst:

341 g $Cr(NO_3)_3.9H_2O$ and 144 O g $Al(NO_3)_2.9H_2O$ were dissolved in 8600 g water at room temperature. The solution is kept under stirring and 10% ammonia solution is added at a uniform rate of 1300 g/h till the pH attains 7.5. The slurry obtained is charged into an autoclave and heated at 90° C. for 2 h and cooled to 50° C. The resulting slurry was filtered and washed with water. The coke obtained was divided into two portion in weight ratio 3:1. The major portion was dried for 2 h at 70° C. and then at 120° C. till constant weight. The dried cake was powdered to a particle size>125 mesh. The second portion was partially dried at 70° C. and mixed with the powder of major portion and extruded into 2.5 mm die pellets or extruded using standard procedures. The extrudes were calcinated at 400° C. for 24 h in $N_2$ atmosphere to get 262 g of co-precipitated catalyst designated as catalyst-A. The catalyst is X-ray amorphous.

The invention claimed is:

1. A process for the preparation of 1,1,1,2-tetrafluoroethane (HFC-134a) from trichloroethylene (TCE), the said process comprising the steps of:
   a) fluorinating trichloroethylene (TCE) with anhydrous hydrogen fluoride (AHF) by contracting with a co-precipitated $Cr_2O_3/Al_2O_3$ catalyst promoted by Zn salt, to obtain an intermediate 2-chloro-1,1,1-trifluoroethane (HCFC-133a), and
   b) fluorinating the product of step (a) with anhydrous hydrogen fluoride (AHF) in presence of co-precipitated $Cr_2O_3/AlO_3$ catalyst promoted by Zinc salt, to yield the required product 1,1,1,2-tetrafluoroethane (HFC-134a), wherein a W/F value is in the range of 80-150;
   wherein the co-precipitated $Cr_2O_3/Al_2O_3$ catalyst promoted by zinc salt is prepared by a process comprising co-precipitation of chromium and aluminum metal hydroxides from corresponding trivalent metal salt solutions using $NH_4OH$, NaOH or KOH as a base and followed by calcination at 400° C. at 24 hours to provide a mixed oxide precatalyst in amorphous form, wherein the ratio of Cr:Al is in the range of 1:1 to 1:14, which is then impregnated using the Equilibrium Adsorption Method with an activity promoting amount of zinc compound, and then thermally treated at 90° C.

2. A process as claimed in claim 1, wherein in steps (a) and (b) the co-precipitated chromia-alumina catalyst contains chromium-aluminum in the atomic ratio in the range of 1:1 to 1:14.

3. A process as claimed in claim 1, wherein in step (a) and (b), the percent of Zinc content in the catalyst, is in the range of 2-12% by weight.

4. A process as claimed in claim 1, wherein in step (a) the mole ratio of AHF and TCE is in the range of 6:1 to 12:1.

5. A process as claimed in claim 1, in step (b) the mole ratio of AHF and HCFC-133a is in the range 4:1 to 15:1.

6. A process as claimed in claim 1, wherein in steps (a) and (b), fluorination is carried out at a temperature in the range of 275-400° C.

7. A process as claimed in claim 1, wherein in steps (a) and (b), the fluorination is carried out in the pressure range of 15 to 210 psig.

8. A process as claimed in claim 1, wherein in step (a) stoichiometric ratio of HF:TCE required to give HCFC 133a is 3:1 and excess of HF is required to obtain maximum conversion and selectivity.

9. A process as claimed in claim 1 wherein in step (b), the ratio of HF:HCFC-133a is in the range of 4:1 to 15:1.

10. A process as claimed in claim 1, wherein in step (b), the ratio of HF:HCFC-133a is in the range of 6:1 to 10:1.

* * * * *